(12) United States Patent
Jivanjee

(10) Patent No.: US 11,577,040 B1
(45) Date of Patent: Feb. 14, 2023

(54) FACE MASK

(71) Applicant: Mehboob Jivanjee, Miami, FL (US)

(72) Inventor: Mehboob Jivanjee, Miami, FL (US)

( * ) Notice: Subject to any disclaimer, the term of this patent is extended or adjusted under 35 U.S.C. 154(b) by 375 days.

(21) Appl. No.: 16/839,856

(22) Filed: Apr. 3, 2020

(51) Int. Cl.
*A61M 16/06* (2006.01)

(52) U.S. Cl.
CPC .... *A61M 16/0666* (2013.01); *A61M 16/0683* (2013.01)

(58) Field of Classification Search
CPC .............. A61M 16/0666; A61M 16/0683
USPC ................................................ 128/207.18
See application file for complete search history.

(56) References Cited

U.S. PATENT DOCUMENTS

| | | | | |
|---|---|---|---|---|
| 5,431,158 A * | 7/1995 | Tirotta | ............. | A61M 16/0488 128/207.14 |
| 5,435,299 A * | 7/1995 | Langman | ............... | A62B 9/003 128/201.13 |
| 6,386,198 B1 * | 5/2002 | Rugless | ............... | A62B 23/025 128/205.25 |
| 6,792,943 B2 | 9/2004 | Kumar et al. | | |
| 8,236,216 B2 * | 8/2012 | Thornton | ............. | A61M 16/06 264/222 |
| 8,365,734 B1 * | 2/2013 | Lehman | ................. | A61B 5/097 128/206.28 |
| 8,960,195 B2 * | 2/2015 | Lehman | .............. | A61M 16/085 128/206.28 |
| 9,272,108 B2 * | 3/2016 | Hu | ........................ | A61M 16/06 |
| 10,589,047 B2 * | 3/2020 | Pedro | .................. | A61M 16/009 |
| 11,020,557 B1 * | 6/2021 | Lehman | ................. | A61B 5/082 |
| 2003/0024533 A1 * | 2/2003 | Sniadach | .............. | A61M 16/06 128/206.28 |
| 2003/0047189 A1 * | 3/2003 | Kumar | .................. | A61M 16/06 128/206.29 |
| 2009/0250061 A1 * | 10/2009 | Marasigan | ............ | A61M 16/06 128/205.13 |

* cited by examiner

*Primary Examiner* — Craig M Schneider
*Assistant Examiner* — David R Deal
(74) *Attorney, Agent, or Firm* — Sanchelima & Associates, P.A.; Christian Sanchelima; Jesus Sanchelima

(57) ABSTRACT

A face mask including a mask assembly and a hole punch assembly is disclosed. The mask assembly includes a face mask which includes a mouth portion and a nose portion. Additionally, the face mask is made of a transparent material allowing other individuals to identify the user wearing the mask. Furthermore, the face mask includes two embodiments of strap attachments. In one embodiment a single strap is used to secure the face mask to a user's head. In another embodiment, two strap loops are used to secure the face mask to a user's ears. The hole punch assembly includes a hole punch rod that is used to create openings on the face mask. The hole punch rod is used to create openings on the mouth portion and nose portion of the face mask. A medical professional may utilize these openings to collect samples from a patient wearing the mask.

11 Claims, 4 Drawing Sheets

FACE MASK

BACKGROUND OF THE INVENTION

1. Field of the Invention

The present invention relates to a face mask and, more particularly, to a face mask that allows for samples to be collected from the mouth or nose of users while the face mask remains worn and attached to the user's face.

2. Description of the Related Art

Several designs for a face mask have been designed in the past. None of them, however, include a face mask including a mask assembly and a hole punch assembly. The mask assembly includes a face mask which includes a mouth portion and a nose portion. Additionally, the face mask is made of a transparent material allowing other individuals to identify the user wearing the mask. Furthermore, the face mask includes two embodiments of strap attachments. In one embodiment a single strap is used to secure the face mask to a user's head. In another embodiment, two strap loops are used to secure the face mask to a user's ears. The hole punch assembly includes a hole punch rod that is used to create openings on the face mask. The hole punch rod is used to create openings on the mouth portion and nose portion of the face mask. As a result, a medical professional may utilize these openings to collect samples from a patient wearing the mask while decreasing their chances of contamination. It is known that medical professionals such as nurses and doctors may often come in contact with individuals that have highly infections virus or diseases such as Covid-19. These medical professionals often have to collect samples from these individuals for testing through their nostrils or mouth area thereby exposing them to risk of contamination. Therefore, there is a need for a face mask that can be worn by medical professionals and patients that can reduce the risk of exposure to highly infectious diseases.

Applicant believes that a related reference corresponds to U.S. Pat. No. 6,792,943 issued for an intubating ventilatory face mask. The face mask provides simultaneous positive pressure ventilation to a patient together with introduction of medical devices shafts into the trachea esophagus, and nasal cavity of a patient. Applicant believes that another related reference corresponds to U.S. patent publication No. 2009/0250061 for a resuscitation face mask. The face mask is used in medical purposes for inducing anesthesia for a patient. Additionally, the mask includes an inflatable/deflatable balloon that allows for a perfect seal between the mask and the patients face. However, the cited references differ from the present invention because they fail to disclose a face mask having a mask assembly and a hole punch assembly. The hole punch assembly is used to make perforations within the mask assembly to allow a medical professional to collect samples for testing through these perforations. As a result, the mask can be used for testing and observation and reduces the risk of exposure to airborne illnesses to the patient and the caretaker.

Other documents describing the subject matter provide for a number of more or less complicated features that fail to solve the problem in an efficient and economical way. None of these patents suggest the novel features of the present invention.

SUMMARY OF THE INVENTION

It is one of the objects of the present invention to provide a face mask that reduces the risk of infection for medical professionals who are in contacted with contaminated individuals.

It is another object of this invention to provide a face mask which is made of a transparent material to allow for testing and observation to be accomplished even while the mask is worn to prevent airborne illnesses from being transmitted.

It is still another object of the present invention to provide a face mask that may be easily mass produced and distributed among medical facilities.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
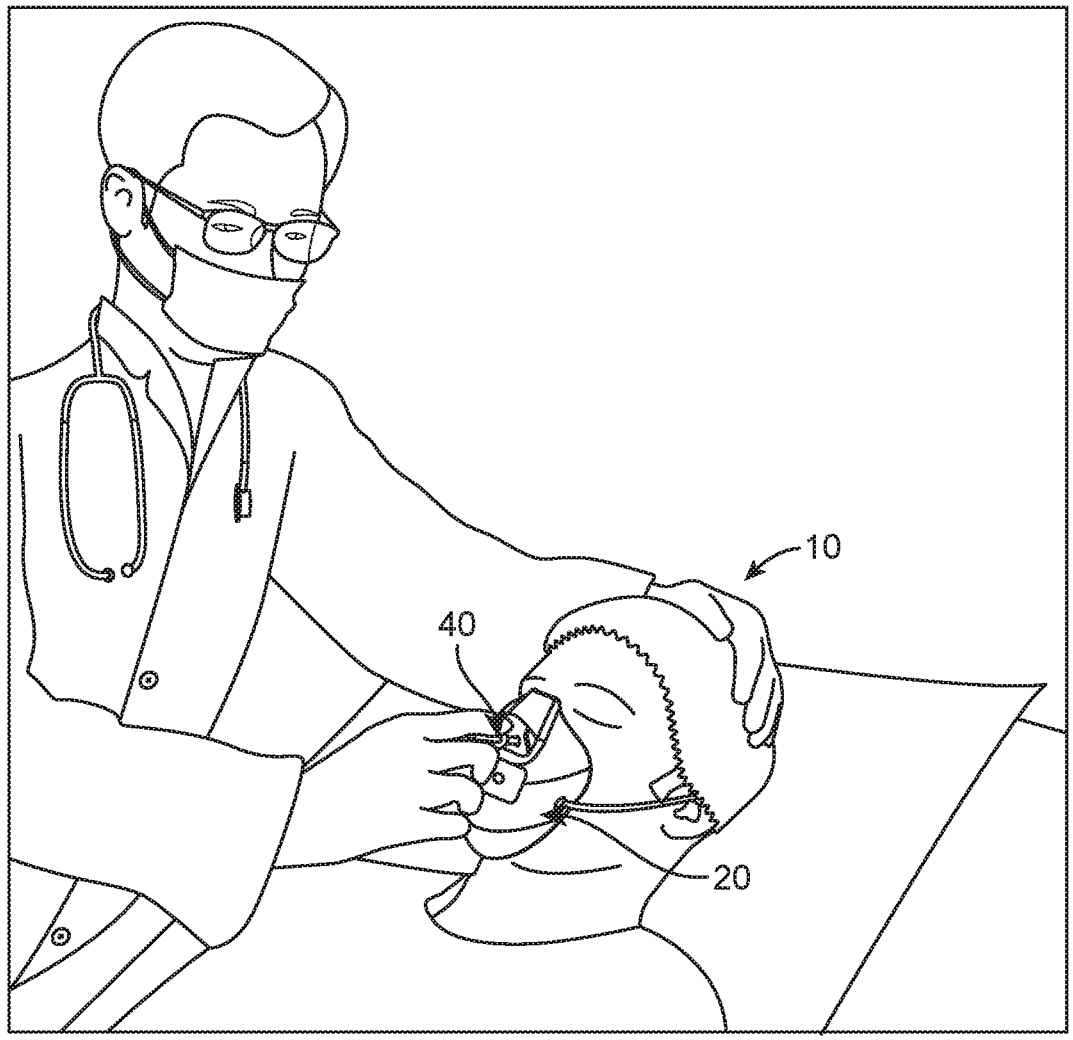
FIG. 1 represents an operational isometric view of face mask 10 in accordance to an embodiment of the present invention.
Figure 2:
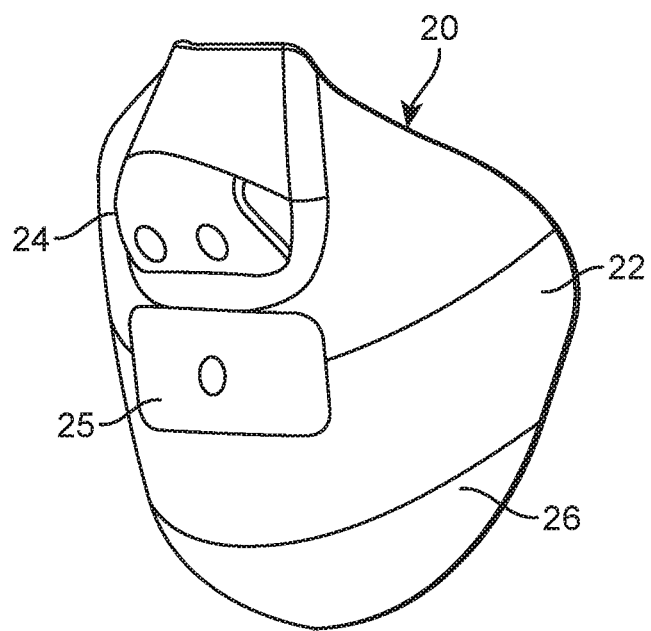
FIG. 2 shows an isometric view of mask assembly 20 in accordance to an embodiment of the present invention.

Referring now to the drawings, where the present invention is generally referred to with numeral 10, it can be observed a face mask 10 that basically includes a mask assembly 20 and a hole punch assembly 40.

Mask assembly 20 includes a mask 22 that is configured to be mounted over a user's face. In one embodiment, mask 22 may be provided in a shape that cooperates with a shape of a user that receives mask 22. Mask 22 may also be made of a transparent material. The transparent nature of mask 22 allows for the observation of a user by a caretaker without the need of having to remove the mask. As a result, there is less risk in the transmittal of airborne diseases. The transparent material may be implemented in such a configuration that it entirely encompasses mask 22. Alternatively, the transparent material may be implanted such that it partially covers mask 22.

Figure 5:
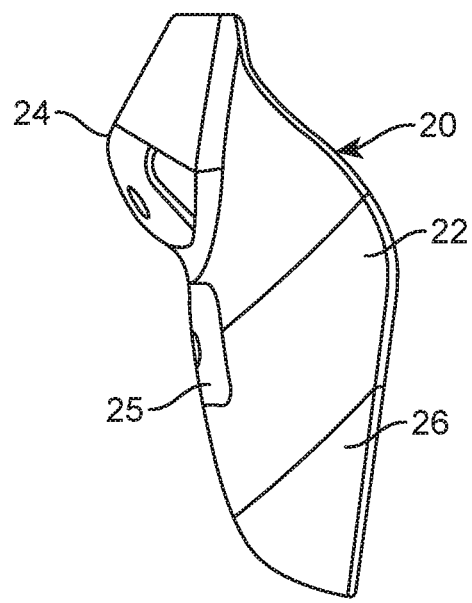
FIG. 5 shows an isometric side view of mask assembly 20 in accordance to an embodiment of the present invention.

Mask 22 further includes a nose portion 24 and a mouth portion 25. Nose portion 24 may coincide with the area of mask 22 that covers a user's nose. Additionally, mouth portion 25 coincides with the area of mask 22 that covers a user's mouth. Nose portion 24 and mouth portion 25 may be manufactured in such way that they entirely cover a user's mouth and nostril area. Additionally, nose portion 24 is an elevated portion that extends beyond mouth portion 25. Nose portion 24 includes a first slanted region and a second slanted region that can best be observed in FIG. 5 of the provided drawings. The first slanted region represents the area of nose portion 24 that covers a bridge of a user's nose. The second slanted region represents the area of nose portion 24 which entirely covers the nostrils of a user's nose. Mouth portion 25 is represented by a flat region that is located beneath nose portion 24. In one implementation, mask 22 snugly fits onto a user's face, the transparent nature of mask 22 allows for a user to continue proper breathing even though mask 22 is covering their face.

Mask 22 further includes side edges 26 having openings 26A. In one embodiment, side edges 26 are located along sides of mask 22 that coincide with a cheek area of a user. Openings 26A are configured to receive at least one strap that is then used to secure mask 22 to the face of a user.

Figure 6:
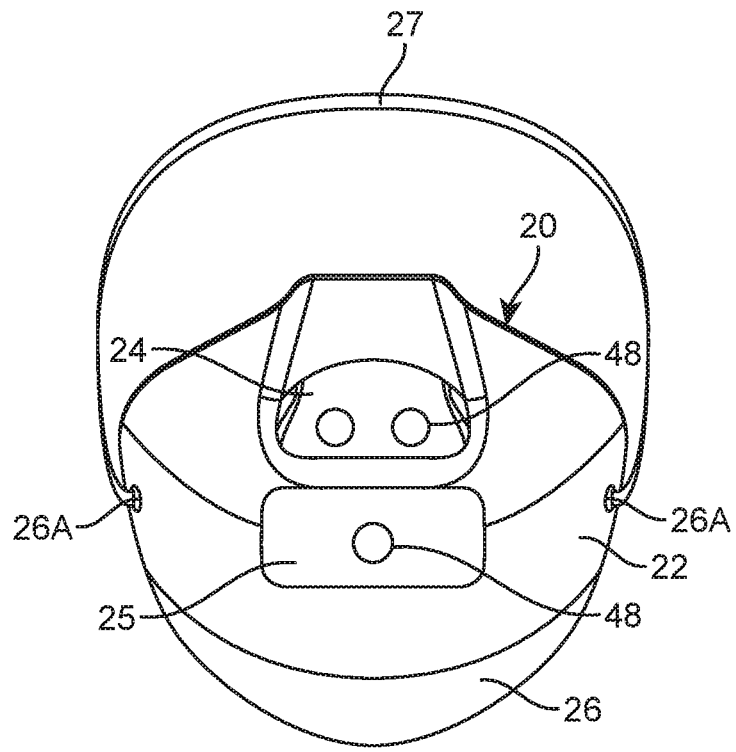
FIG. 6 illustrates a front isometric view of mask assembly 20 with a single strap 27 in accordance to an embodiment of the present invention.

In one implementation, openings 26A receive a single strap 27 as observed in FIG. 6 of the provided drawings. Single strap 27 as known in the art of masks, may be made of an elastic material. In this implementation, single strap 27 is securely tied to openings 26A and configured to be wrapped around a user's head to then be mounted. The length of single strap 27 may vary with the needs of various users.

Figure 7:
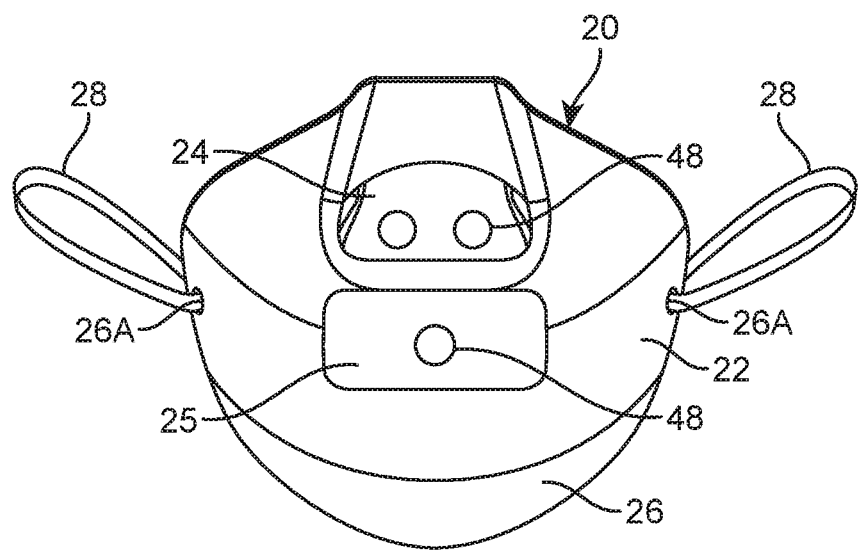
FIG. 7 illustrates a front isometric view of mask assembly 20 with double straps 28 in accordance with another embodiment of the present invention.

In another implementation, openings 26A receive double straps 28 which as observed in FIG. 7 of the provided drawings. In this implementation, each of openings 26A receive a strap to create a double looped system. Each loop is then received by an ear of a user to create a mounting means for mask 22 onto the face of a user. Double straps 28 may also be made of an elastic material and securely tied to openings 26A.

Hole punch assembly 40 includes a tubing 42 provided with a first opening and a second opening. In one implementation, tubing 42 is provided as an elongated cylindrical tube. Additionally, tubing 42 may be made of a clear plastic and flexible material. This allows a caretaker to observe elements that may be passing through tubing 42. Furthermore, tubing 42 includes a plate 44 that is mounted to an outer surface of tubing 42. In one embodiment, plate 44 is circular in shape and tubing 42 is inserted through plate 44. Plate 44 may be mounted in such a configuration that it may freely move up and down the outer surface of tubing 42. Plate 44 serves as a guide to aid a caretaker in placing tubing 42 over nose area 24 and mouth area 25.

Figure 3:
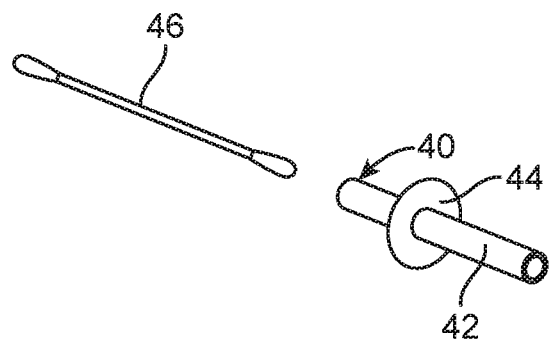
FIG. 3 illustrates an isometric view of hole punch assembly 40 in accordance to an embodiment of the present invention.
Figure 4:
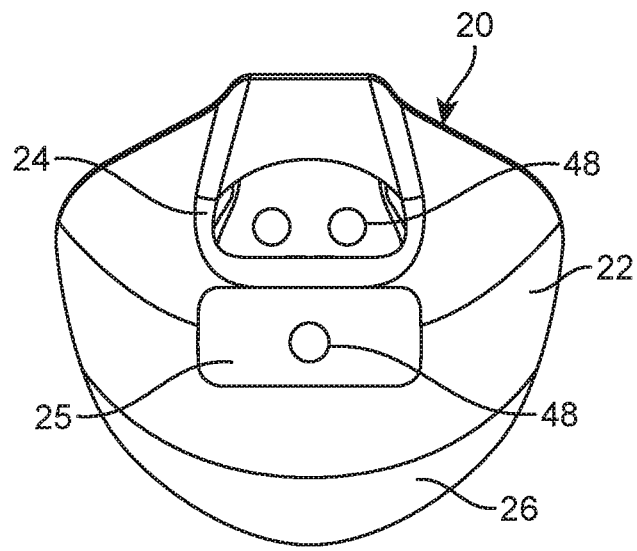
FIG. 4 is a representation of a front view of mask assembly 20 having perforations 48 in accordance to an embodiment of the present invention.

In one embodiment, plate 44 is used to position tubing 42 over nose area 24 and mouth area 25. A swab 46 is then inserted within tubing 42 as observed in FIG. 3 of the provided specifications. Swab 46 as known in the art may be a sterile rod provided with a cotton material at a distal end. Additionally, swab 46 then acts as a punctuating member that receives a force to puncture perforations 48 into mask 22. These perforations 48 may be observed in FIG. 4 of the provided drawings. Tubing 42 may be provided with a length that is less than swab 46 thereby allowing swab 46 to pass entirely through tubing 42 to create the desired perforation.

Swab 46 is then inserted through perforations 48 in order to collect samples from a user. This method of collecting samples prevents the transmittal of airborne diseases from a caretaker to a patient. In one implementation, a single perforation is made on mouth portion 25 of a user to collect a sample from within a user's mouth. In another implementation, two perforations are made on nose portion 24. Each perforation providing access within a user's nostril area. A sample may then be collected from within the user's nostrils. A total of three perforations may be made onto mask 22 for the collecting of samples.

Face mask 10 further includes a method. This method includes placing mask 22 onto a user's face. In the present implementation, the user is a patient of a caretaker. The method further includes positioning hole punch assembly 40 over nose portion 24 or mouth portion 25. Plate 44 is utilized as a guiding mechanism to ensure that hole punch assembly 40 is positioned correctly on its desired location. Furthermore, the method includes puncturing swab 46 through nose portion 24 or mouth portion 25 to create a perforation. This action is done while swab 46 is housed within tubing 42 thereby reducing the contamination of any bacteria to the caretaker. Finally, the method includes collecting a sample from a user. This method allows for the sample to be safely collected from a user while drastically minimizing a caretaker's risk of exposure to an airborne illness.

The present invention 10 may be used in a variety of situations to aid a caretaker in evaluating a patient. In one implementation, face mask 10 may be used while a patient is standing up or laying down on a bed. Additionally, it should be understood, face mask 10 does not need single straps 27 or double straps 28 for operational use. In one embodiment, a caretaker may manually hold face mask 10 to a patient's face to then take a sample from the patient. Furthermore, the transparency of face mask 10 allows the caretaker to observe the patient's symptoms that may otherwise not be noticed by a traditional mask.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A system for a face mask, comprising:
   a) a mask assembly including a face mask made of a transparent material, said face mask including a mouth portion and a nose portion, wherein said nose portion is an elevated portion protruding above said mouth portion when viewed from the side, said face mask including side edges having openings; and
   b) a hole punch assembly including a tubing with a first and second opening, a plate mounted to an outer surface of said tubing, a swab inserted through said tubing, said hole punch assembly is configured to be placed over said mouth portion or said nose portion, said swab is adapted to be actuated through said tubing to create a perforation on said mouth portion or said nose portion.

2. The system for a face mask of claim 1 wherein said openings receive a single strap configured to be wrapped around a user's head, said single strap being made of an elastic material.

3. The system for a face mask of claim 1 wherein said openings receive double straps configured to be mounted to a user's ear, said double straps being made of an elastic material.

4. The system for a face mask of claim 1 wherein said nose portion includes a first slanted region and a second slanted region.

5. The system for a face mask of claim 1 wherein said tubing is inserted through said plate, said plate moving freely along said outer surface.

6. The system for a face mask of claim 1 wherein said tubing includes a length that is less than a length of said swab.

7. The system for a face mask of claim 1 wherein said swab includes a cotton material on a distal end.

8. The system for a face mask of claim 1 wherein said nose portion includes two perforations.

9. The system for a face mask of claim 1 wherein said mouth portion includes a single perforation.

10. A method comprising:
   a) providing a system for a face mask according to claim 1;
   b) placing said face mask on a user's face;
   c) positioning said hole punch assembly over said mouth portion or said nose portion;
   d) puncturing said swab through said mouth portion or said nose portion to create said perforation; and
   e) collecting a sample from said user.

11. A system for a face mask, comprising:
   a) a mask assembly including a face mask made of a transparent material, said face mask including a mouth portion and a nose portion, said nose portion being an elevated portion which extends beyond said mouth portion, wherein said mouth portion is a flat portion located beneath said nose portion when viewed from the side, said face mask having side edges which include side openings, said side openings each receiving a strap configured to be received by a user's ears; and
   b) a hole punch assembly including an elongated cylindrical tube with a first opening and a second opening, said elongated cylindrical tube having a guiding plate that is circular in shape mounted to an outer surface, wherein said guiding plate moves freely along said elongated cylindrical tube, said elongated cylindrical tube receiving a swab from said first opening, wherein said guiding plate and said elongated cylindrical tube is configured to be placed on said mouth portion or said nose portion of said face mask, said swab guided within said elongated cylindrical tube is adapted to create a perforation within said mouth portion and said nose portion.

* * * * *